(12) United States Patent
Torii

(10) Patent No.: US 7,833,155 B2
(45) Date of Patent: Nov. 16, 2010

(54) ENDOSCOPIC PASSAGE CONFLUENT STRUCTURE

(75) Inventor: Yuichi Torii, Saitama (JP)

(73) Assignee: Fujinon Corporation, Saitama-shi (JP)

( * ) Notice: Subject to any disclaimer, the term of this patent is extended or adjusted under 35 U.S.C. 154(b) by 0 days.

(21) Appl. No.: 11/713,707

(22) Filed: Mar. 5, 2007

(65) Prior Publication Data

US 2007/0204890 A1 Sep. 6, 2007

(30) Foreign Application Priority Data

Mar. 6, 2006 (JP) .................. P2006-058821

(51) Int. Cl.
*A61B 1/12* (2006.01)
*A61B 1/00* (2006.01)

(52) U.S. Cl. .................. 600/157; 600/153; 600/156

(58) Field of Classification Search ............ 600/153, 600/156–158; 604/43, 284; 285/127.2, 128.1, 285/129.1, 131.1, 129, 130
See application file for complete search history.

(56) References Cited

U.S. PATENT DOCUMENTS

| 4,557,261 | A | * | 12/1985 | Rugheimer | ............ | 604/533 |
| 4,784,119 | A | | 11/1988 | Matsuura | | |
| 4,860,731 | A | * | 8/1989 | Matsuura | ............ | 600/157 |
| 5,685,823 | A | * | 11/1997 | Ito et al. | ............ | 600/127 |
| 5,735,793 | A | * | 4/1998 | Takahashi et al. | ............ | 600/153 |
| 6,620,096 | B2 | * | 9/2003 | Arai et al. | ............ | 600/156 |

FOREIGN PATENT DOCUMENTS

| DE | 10 2004 029 099 A1 | 1/2005 |
| JP | 58-86131 A | 5/1983 |
| JP | 7-79911 A | 3/1995 |
| JP | 8-10216 A | 1/1996 |
| JP | 10-219806 A | 8/1998 |
| JP | 2003-328750 A | 11/2003 |
| JP | 3678614 A | 5/2005 |

* cited by examiner

*Primary Examiner*—Linda C Dvorak
*Assistant Examiner*—Alireza Nia
(74) *Attorney, Agent, or Firm*—Birch, Stewart, Kolasch & Birch, LLP

(57) ABSTRACT

An endoscopic flow-passage confluent structure that connects a gas-feed tube and a liquid-feed tube provided in an endoscope to a confluent tube communicating with an ejection nozzle arranged at a tip of an insertion portion of the endoscope and for ejecting a cleaning fluid toward a viewing window of the endoscope, the structure comprising: (i) a passage connection member having one end opened with two upstream-passage receiving bores in which the gas-feed and liquid-feed tubes are respectively inserted and fixed, other end opened with one downstream-passage receiving bore, and an intermediate region that communicates the upstream-passage receiving bores with downstream-passage receiving bore and comprises a passage confluent space having a diameter increasing in a taper-form in a direction of from the downstream-passage receiving bore toward the upstream-passage receiving bores; and (ii) a coupler pipe having one end connected to the downstream-passage receiving bore and other end connected with a base of the confluent tube.

4 Claims, 5 Drawing Sheets

ENDOSCOPIC PASSAGE CONFLUENT STRUCTURE

BACKGROUND OF THE INVENTION

1. Field of the Invention

The present invention relates to an endoscopic passage-confluent structure that joins a liquid feed tube and a gas feed tube together into connection to a confluent tube communicating with an ejection nozzle, in a cleaning mechanism arranged in an endoscope and for feeding a cleaning fluid, of a liquid or a gas, to a viewing window arranged at the tip of an insertion portion thereof.

2. Description of the Related Art

The endoscope, particularly for medical use, is provided with a viewing window at the tip of its insertion portion in order to observe the body interior. During endoscopic examination, the viewing window is possibly contaminated with body fluids, etc. For this reason, a cleaning mechanism is provided for the viewing window. The cleaning mechanism is constructed with an ejection nozzle arranged nearby the viewing window, a feed passage of a cleaning fluid, e.g. a cleaning liquid or a pressurized gas, leading to the ejection nozzle, and a control mechanism for control of feeding the cleaning fluid. When the viewing window is contaminated, a cleaning liquid is issued at the ejection nozzle to clean away the contaminants on the viewing window, followed by feeding a pressurized gas to the ejection nozzle. This can remove the droplets adhered to the viewing window. Here, the cleaning water can use water while the pressurized gas can be air. This makes it possible to keep well the field of sight through the viewing window without taking the insertion portion out of the body interior.

The control mechanism can be operated with a finger of the hand gripping the body control portion of the endscope. Specifically, this is formed by water-feed and gas-feed valves, or a gas/water feed valve formed with water-feed and gas-feed valves in one body. For this reason, the feed passage is arranged with the water and gas tubes respectively connected to the water-feed and gas-feed valves. Those tubes are both in communication with the ejection nozzle. Here, because cleaning water and pressurized air are fed in order instead of being ejected at the same time, the ejection nozzle is usually structured for feeding both water and gas, in order to reduce the diameter of the insertion portion. There is an arrangement that the water-feed and gas-feed tubes are joined together at the inside of the body control portion by the request of reducing the diameter of the insertion portion. For example, Japanese Patent No. 3,678,614 discloses a structure that the confluent tube is provided at the tip of the insertion portion by joining the water-feed tube and the gas-feed tube together at the inside of the body control portion.

This Japanese Patent No. 3,678,614 discloses two types of conduit confluent structures. Firstly, there is a branch structure that a bend tube is connected to an intermediate point of one tube provided straight. In this case, any one of the water-feed and gas-feed tubes is connected to the bend tube while the other is to one end of the straight tube wherein the confluent tube is connected to the other end of the straight tube. Meanwhile, the other confluent structure uses a confluent member in a block form. The confluent member is formed with a penetrating flow passage extending straight. Meanwhile, a flow passage, parallel with the penetration flow passage, is formed extending from one end to intermediate point of the confluent member. By opening a flow passage orthogonal to the same, confluence is provided with the penetration flow passage. Consequently, the confluent member has two openings of flow passages at its one end and one opening of flow passage at the other end. Water-feed and gas-feed tubes are respectively connected to the two flow passages at the one end while a confluent tube is connected to the other end.

In using a branch structure or a block-formed confluence member, the confluence structure in Japanese Patent No. 3,678,614 is structurally provided by forming one straight flow passage and joining the other flow passage with the straight flow passage. For this reason, because fluid flow is straight through one of the two conduits connected to the confluence member, the resistance to flow is less thus forming a smooth flow. However, the flow passage joined to the straight flow passage is bent sharply in its route and hence considerably great in the resistance to flow, thus resulting in a conspicuous pressure loss with a turbulent flow at the confluent point. Therefore, a considerable great difference encounters between the fluids flowing through the two flow passages.

In the branch structure, the conduit is weak at the connection because of providing a through hole in the straight conduit and connecting a bend conduit by means of soldering or welding. Here, the branch conduit is provided within the body control portion wherein other members are arranged within the body control portion. For example, there is a possibility that the branch tube is urged by a manipulation-tool receiving channel, various operation wires, etc. Thus, the connection is possibly broken or cracked by the reaction of such an external force. Because of a cleaning liquid used as a cleaning fluid, the liquid if leaks through the broken point would cause a contamination in the interior of the body control portion.

Meanwhile, where using a block-formed confluent member, there is a no fear of breakage or the like. However, because such a block structure requires a greater size as compared to the branch structure, there is a difficulty in obtaining a sufficient space for arrangement in the body control portion. Besides, there is a fear that the block urges the received members, such as light guides and cables, provided in a manner passing through the body control portion, into a disconnection.

SUMMARY OF THE INVENTION

The present invention has been made in view of the foregoing points, and it is an object thereof to provide an endoscopic flow-passage confluent structure small and compact in size but highly strong so that smooth flow can be formed with reduced resistance through any of the flow passages that are joined together.

In order to achieve the foregoing object, the present invention is an endoscopic flow-passage confluent structure that connects a gas-feed tube and a liquid-feed tube provided in an endoscope to a confluent tube communicating with an ejection nozzle arranged at a tip of an insertion portion of the endoscope and for ejecting a cleaning fluid toward a viewing window of the endoscope, the structure comprising: (i) a passage connection member having one end opened with two upstream-passage receiving bores in which the gas-feed and liquid-feed tubes are respectively inserted and fixed, other end opened with one downstream-passage receiving bore, and an intermediate region that communicates the upstream-passage receiving bores with downstream-passage receiving bore and comprises a passage confluent space having a diameter increasing in a taper-form in a direction of from the downstream-passage receiving bore toward the upstream-passage receiving bores; and (ii) a coupler pipe having one end connected to the downstream-passage receiving bore and other end connected with a base of the confluent tube.

The coupler pipe attached in the downstream-passage receiving bore is to selectively feed a gas of from the gas-feed tube and a liquid of from the liquid-feed tube. The feed control of the cleaning fluid is preferably by a finger of the hand gripping the body control portion. For this reason, a valve or switch is provided in the body control portion, to control the feed of cleaning fluid by means of switch operation. Where a valve is provided to control the feed of cleaning fluid, it is usual to provide one gas-feed/water-feed valve though gas-feed and water-feed valves can be arranged separately. The passage connection member, for joining together the two tubes of from the valve(s), can be provided inside the body control portion where is coupled with a base of an insertion portion in order to reduce the diameter of the insertion portion though can be arranged in the insert part in a position close to the boundary between a non-rigid portion and an angle portion. The gas-feed and liquid-feed tubes can employ such a structure that a part thereof is formed by a rigid pipe to connect, at an intermediate point, with a flexible tube as required. However, from a viewpoint of extending the passage, it is preferred to structure it by a flexible tube, particularly flexible in bending and not expandable/shrinkable.

Where provided in the body control portion, these conduits can be formed of a material that is bendable but highly rigid. Meanwhile, the confluent tube can be formed of a tubular material. The confluent tube is desirably flexible to a further extent because to be passed through the insertion portion. The passage connection member is usually formed by a rigid member. The passage connection member is connected with conduits at its front and rear ends, i.e. connected with one conduit at one end and two, or gas-feed and water-feed, conduits at the other end. The one conduit and the two conduits join together within the passage connection member. Consequently, the confluent space is provided by a cavity broader on the side closer to the two conduits than on the side closer to the one conduit. For this reason, the passage confluent space is made in a form having a diameter increasing in a taper form in a direction of from the downstream-passage receiving bore to the upstream-passage receiving bores.

Here, in forming the passage connection member with a cavity having a diameter increasing in a taper form and serving as a conduit confluent space, forming is possible by drilling with a cutting tool, such as a drill, inserted through the downstream-passage receiving bore. Meanwhile, the downstream-passage receiving bores, for connecting two conduits, can be formed by use of a similar tool. Here, there is a need to provide a downstream-passage receiving bore with a broader opening, for the convenience sake of forming a conduit confluence space. The downstream-passage receiving bore is connected with the confluent conduit. Because the confluence conduit at its base is connected with a coupler pipe, by matching the outer diameter of the coupler pipe to the diameter of the downstream-passage receiving bore, the diameter of the downstream-passage receiving bore can be established regardless of the outer diameter of the confluence conduit. Accordingly, the upstream flow passage is constituted by the gas-feed and liquid-feed tubes while the downstream flow passage is by the confluence conduit and the coupler pipe.

In the case the gas-feed and liquid-feed tubes constituting the upward flow passage is formed by a flexible tube, those are fixed in the two upstream-passage receiving bores of the passage connection member by means of an adhesive or the like. On the contrary, the downstream-passage receiving bore of the passage connection member is fixed with the coupler pipe constituting part of the downward flow passage. It can be fixed by screwing, bonding or so. Meanwhile, the tip of the coupler pipe can be connected by means of brazing (or soldering), press-fit or so.

DETAILED DESCRIPTION OF THE INVENTION

Figure 1:
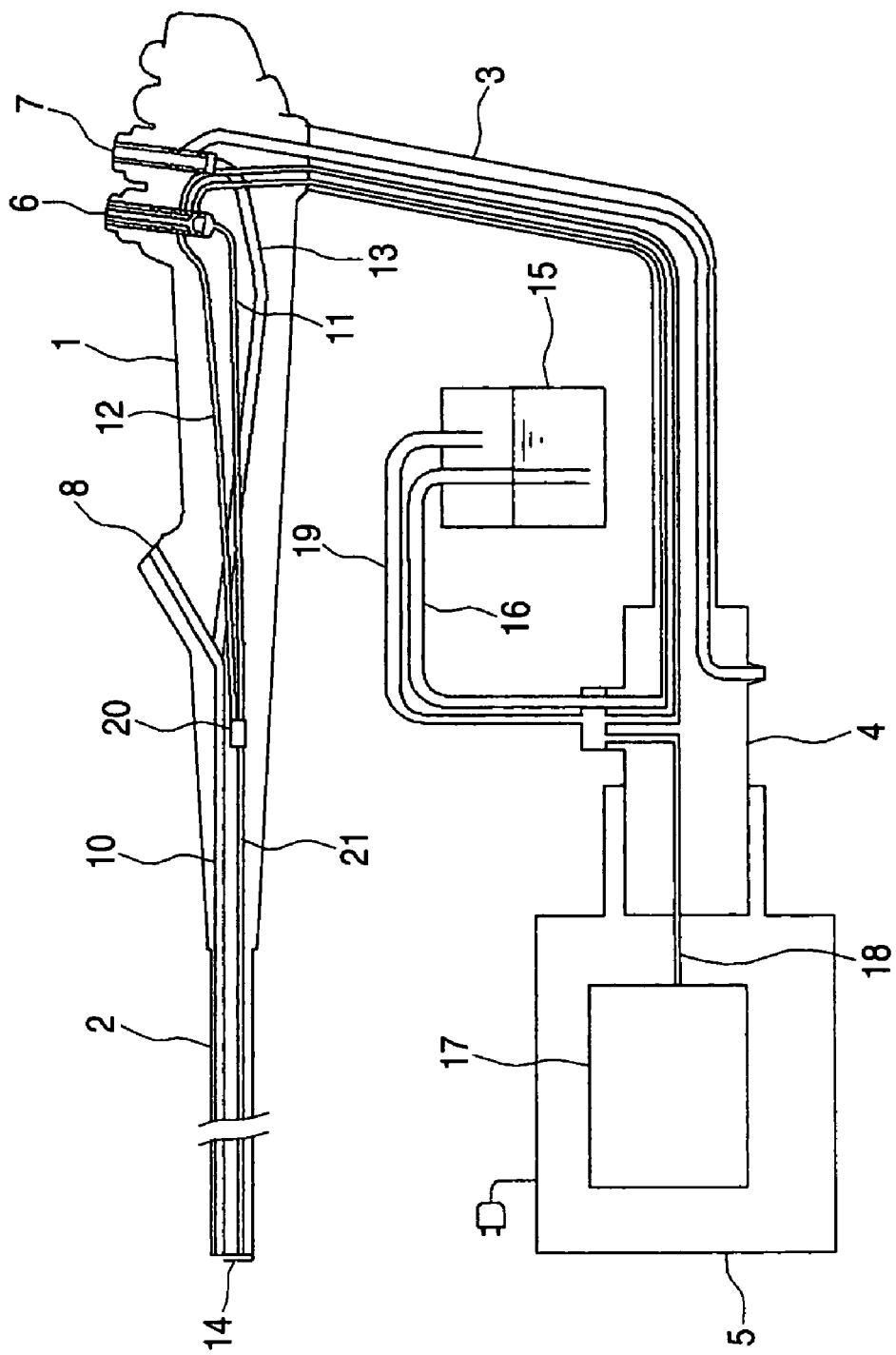
FIG. 1 is a structural explanatory view of various conduits provided in an endoscope.

Based on the drawings, explanation will now made on an embodiment according to the present invention. FIG. 1 shows a schematic arrangement of conduits provided in an endoscope. In the figure, reference numeral 1 designates a body control portion, 2 an insertion portion to a body cavity, etc., and 3 a universal cord. The universal cord 3 is provided with a connector 4 at the tip thereof. The connector 4 is removably connected to a control unit 5 (generally, including a light source and a video-signal processing circuit). The body control portion 1 is arranged with a gas/water feed valve 6 and a suction valve 7, and also with a manipulation-tool guide 8.

The endoscope includes mainly conduits including a manipulation-tool receiving channel 10, a gas-feed tube 11, a liquid-feed tube 12 and a suction passage 13. The manipulation-tool receiving channel 10 has a base communicating with the manipulation-tool guide 8 and a tip opening in a tip face of the insertion portion 2. The gas-feed and liquid-feed tubes 11, 12 both communicate with the gas/water feed valve 6, whose tip ends are directed, as they are or by being joined together, to a view window, not shown, by means of an election nozzle 14. The gas-feed and liquid-feed tubes 11, 12 have respective bases, with respect to the gas/water feed valve 6, extending up to the connector 4 of the universal cord 3. The liquid feed tube 12 is connected to a water pipe 16 of from a water tank 15.

The control unit 5 is furnished with a pneumatic pump 17. The pneumatic pump 17 has an air tube 18 removably connected to the gas feed tube 11. The gas-feed tube 11 is structured connectable also with a pressurizing pipe 19 for applying pressure onto the liquid surface in the water tank 15. Furthermore, the suction passage 13, in the body control portion 1, joins with the manipulation-tool receiving channel 10 and leads to the connector 4 of the universal cord 3 by way of the suction valve 7, thus being removably connected to a suction source, not shown.

The gas-feed and liquid-feed tubes 11, 12 are respectively structured by a tube material flexible in bending. The two feed tubes 11, 12 are connected to a confluent tube 21, formed as a single conduit, through a passage connection member 20. Accordingly, the gas-feed and liquid-feed tubes 11, 12 constitute an upstream flow passage while the confluent tube 21 a downstream flow passage. The passage connection member 20, communicating between the foregoing flow passages, is arranged in the body control portion 1, in a position forward of the connection of the manipulation-tool receiving channel 10 with the manipulation-tool guide 8.

Figure 2:
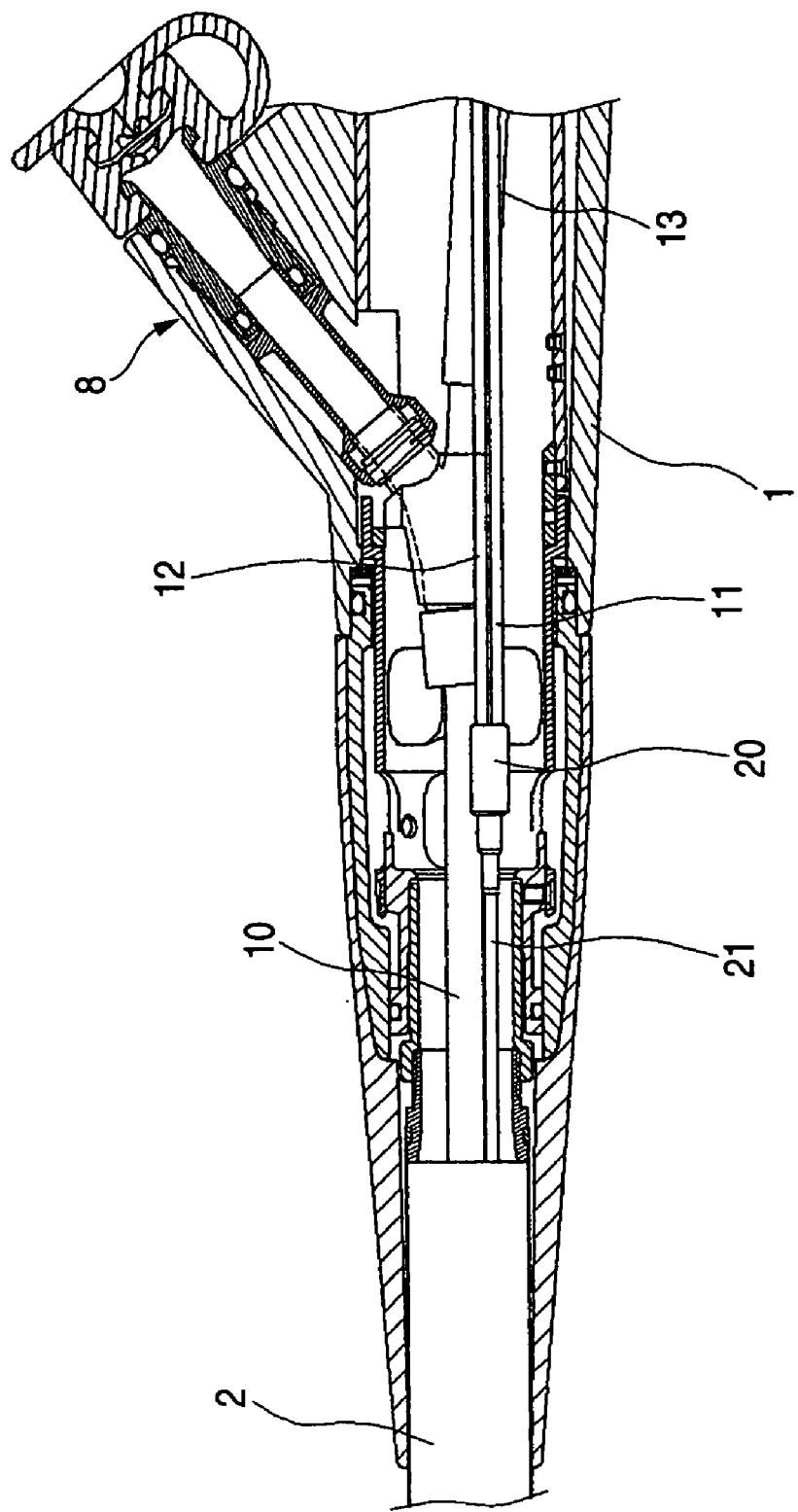
FIG. 2 is a sectional view of a body control portion of the endoscope, showing by omitting part of members received.
Figure 3:
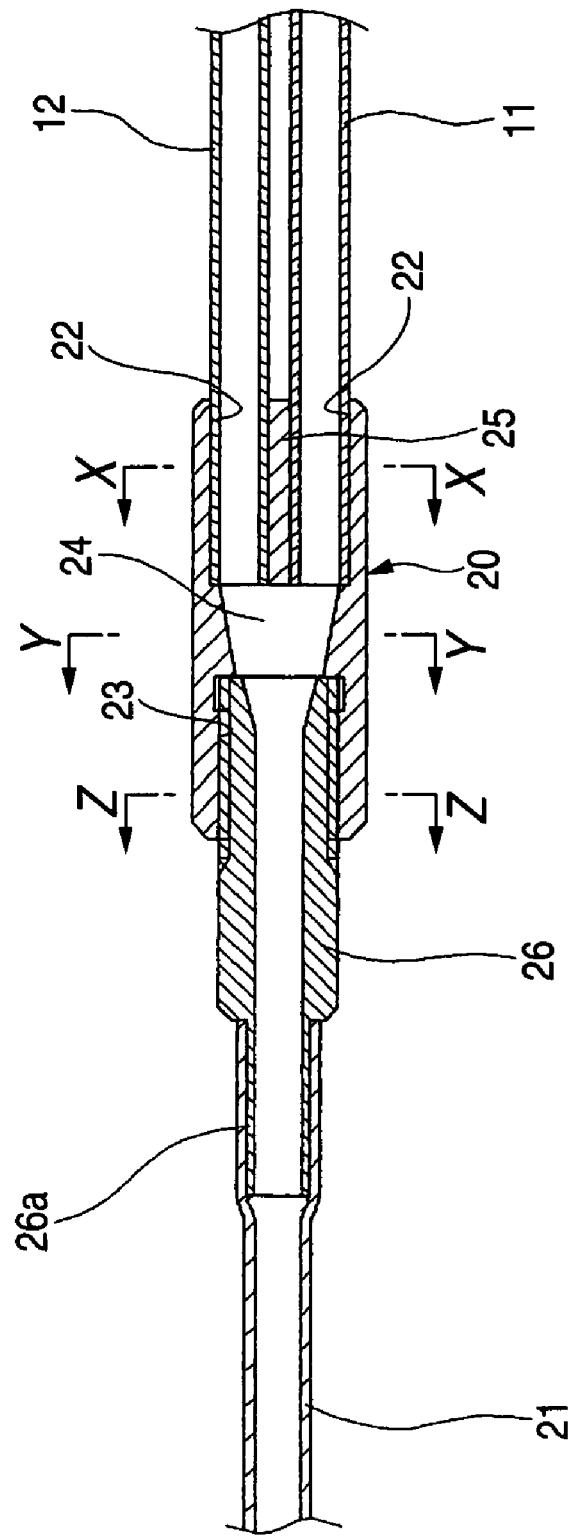
FIG. 3 is a sectional view of a passage connection member connecting between gas-feed and liquid-feed tubes and the confluent tube.

The passage connection member 20 is to join, into one confluent tube 12, the two, or gas-feed and liquid-feed, tubes 11, 12 extending from the gas/water valve 6, as shown in FIGS. 2 and 3. The confluent tube 21 extends in the insertion portion 2 and opens, at its tip, in the ejection nozzle 14. The passage connection member 20 accordingly has one end formed with two upstream-passage receiving bores 22, 22 and the other end formed with one downstream-passage receiving bore 23. The passage connection member 20 has an intermediate portion forming a tapered passage-confluent space 24 having an inner diameter increasing, at a predetermined angle, from the downstream-passage receiving bore 23 to the two upstream-passage receiving bores 22, 22. Note that light guides, signal cables, angle-operation wires, etc. are received in the body control portion 1, which elements are omitted to show in FIG. 2.

In forming such upstream-passage receiving bores 22 and downstream-passage receiving bores 23, 24 in the passage connection member 20, a downstream-passage receiving bore 23 is first formed in the passage-connection member 20 in a region of from one end to an intermediate point thereof. The downstream-passage receiving bore 23 is provided greater than the outer diameter of the confluent tube 21, which moreover is formed as a threaded bore. Then, by inserting a drill in the downstream-passage receiving bore 23 at its end in a direction obliquely upward, a cavity is formed extending obliquely upward from the end of the downstream-passage receiving bore 23. In the drilling, it is possible to use the same tool as used in opening the upstream-passage receiving bores 22 in the passage connection member 20 at the other end thereof. Using the drill, a passage is formed obliquely downward. Furthermore, a similar passage is also formed centrally of the downstream-passage receiving bore 23. Incidentally, the procedure of working is not limited to the above, i.e. any of working steps may be performed earlier in the order. This forms a cavity providing a passage confluent space 24. Incidentally, the passage confluent space 24 is desirably finished smooth in its peripheral inner wall surface. Thereafter, two upstream-passage receiving bores 22 are formed in the passage connection member 20 at the other end, to make the both upstream-passage receiving bores 22 communicate with the passage confluent space 24. Here, a partition wall 25, interposed between the two upstream-passage receiving bores 22, 22, can be formed small in thickness.

In the passage connection member 20 thus structured, flexible tubes respectively forming the gas-feed tube 11 and the liquid-feed tube 12 are connected to the two upstream-passage receiving bores 22. Meanwhile, the confluent tube 21 is connected to the downstream-passage receiving bore 23. Here, because the upstream-passage receiving bore 22 has a diameter slightly greater than the outer diameter of the gas-feed and liquid-feed tube 11, 12, the gas-feed and liquid-feed tubes 11, 12 are inserted and fixed therein by use of an epoxy adhesive, for example. On the contrary, the downstream-passage receiving bore 23 has a diameter considerably greater than the outer diameter of the confluent tube 21. Accordingly, the confluent tube 21 is not directly inserted in the downstream-passage receiving bore 23 but connected therewith by use of a coupler pipe 26. The coupler pipe 26 has a tip made as a tube connection 26a over which the confluent tube 21 is fit. The tube connection 26a is firmly fit with the confluent tube 21, say, through an epoxy adhesive. The coupler pipe 26 and the confluent tube 21 form a downstream flow passage. Meanwhile, a thread is formed in the outer peripheral surface at the base of coupler pipe 26, to be screwed and fixed in a downstream-passage receiving bore 23 made as a threaded bore. Note that firm secure is done by applying an adhesive to the thread fitting.

Accordingly, the upstream-passage receiving bore 22 of the passage connection member 20 is made in a size to directly receive therein the gas-feed tube 11 and liquid-feed tube 12, thus being reduced in its diameter. As for the downstream-passage receiving bore 23, the confluent tube 21 is not directly inserted to the passage confluent member 20 but connected to the downstream-passage receiving bore 23 through the coupler pipe 26. Due to this, the downstream-passage receiving fore 23 can be made with a diameter required to form the passage confluent space 24 without relying upon the outer diameter of the confluent tube 21. Therefore, the passage confluent space 24 can be easily formed. Moreover, the passage confluent space 24 can be easily finished into a smooth inner wall. Naturally, by smoothly forming the upstream-passage receiving bore 22 of the passage connection member 20 and the interior of the coupler pipe 26 constituting the downstream flow passage, the fluid resistance through those passages can be reduced to the minimal degree. Furthermore, there is provided an inclination at a moderate angle in the flow passage extending from the upstream-passage receiving bores 22 to the downstream-passage receiving bore 22 (specifically, interior of the coupler pipe 26). Because of no sharp bend in the flow passage, the resistance of the cleaning fluid to the pipe is reduced in the region of from the gas-feed and liquid-feed tubes 11, 12 to the confluent tube 21, thus reducing the pressure loss to the minimal degree.

Figure 4:
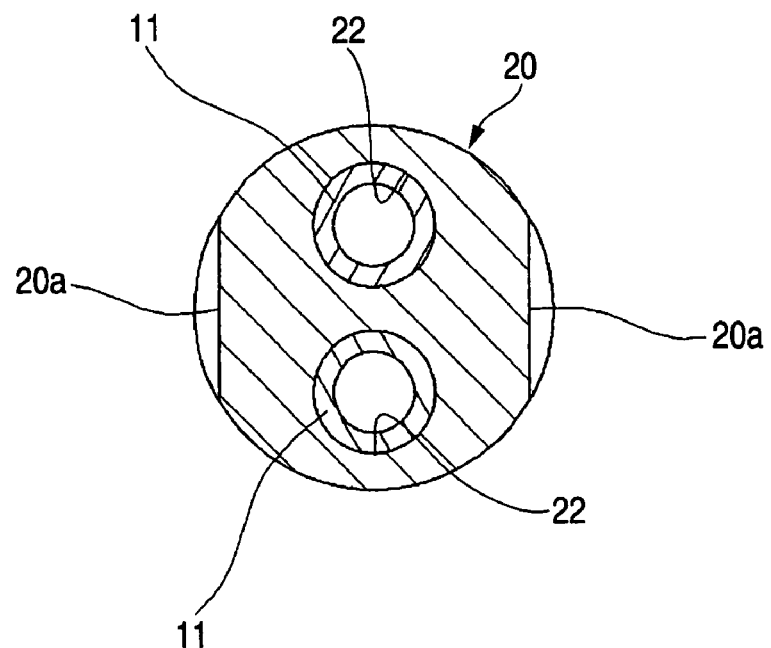
FIG. 4 is a sectional view taken on X-X in FIG. 3.
Figure 5:
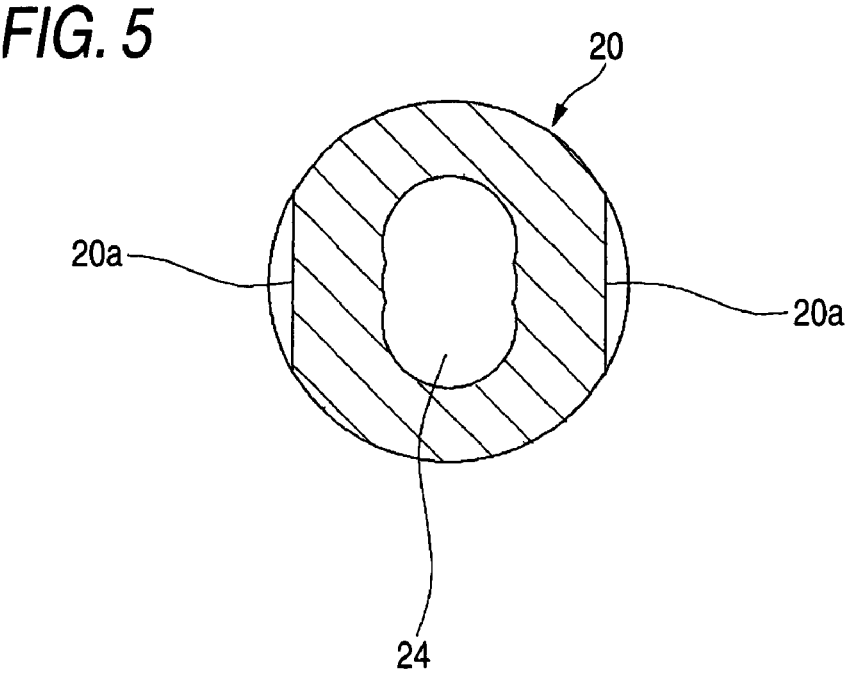
FIG. 5 is a sectional view taken on Y-Y in FIG. 3.
Figure 6:
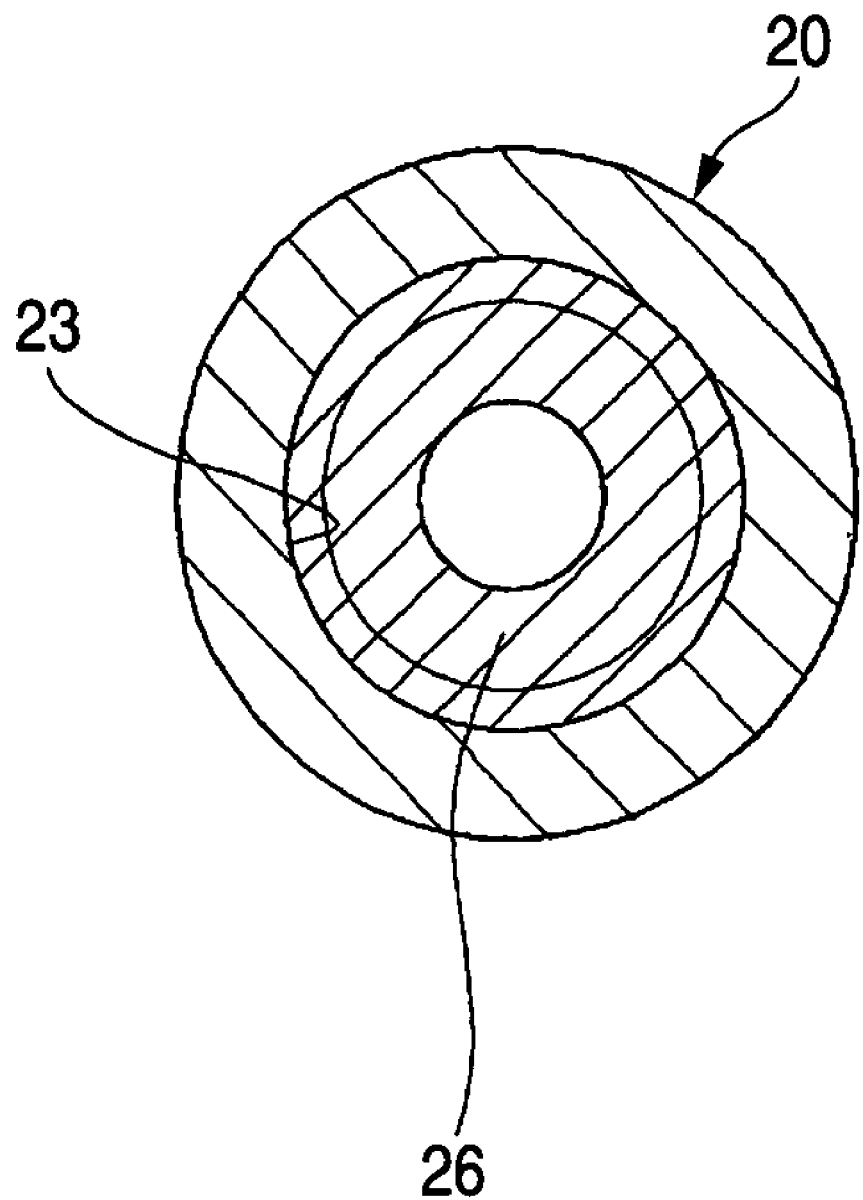
FIG. 6 is a sectional view taken on Z-Z in FIG. 3.

The passage connection member 20 is formed of a metal, thus being formed with cutouts 20a, 20a in a region of from the end having the openings of the upstream-passage receiving bores 22 to the passage confluent space 24, as shown in FIGS. 4 and 5. Meanwhile, as shown in FIG. 6, the region the downstream-passage receiving bore 23 is formed is made in a cylindrical form. This makes it possible to make the passage connection member 20 compact, thus saving the space within the body control portion 1. Meanwhile, because of reduced concavo-convexes and steps in the outer surface, no strong compression forces acts even in case a relative movement occurs with the various members inserted through the body control portion 1.

In the confluence of endoscopic flow passages, the passage connection member serves to join the gas-feed and liquid-feed tubes into a confluence tube, within which member there is formed a flow passage that one flow passage branches into two at a predetermined angle. Accordingly, there is less resistance-along-tube in the flow of from the gas-feed tube to the confluent tube and in the flow of from the liquid-feed tube to the confluent tube, thus suppressing the pressure loss to a minimal degree and making those two flows smooth. Furthermore, the passage connection member can be structured small and compact in size.

The entire disclosure of each and every foreign patent application from which the benefit of foreign priority has been claimed in the present application is incorporated herein by reference, as if fully set forth.

What is claimed is:

1. An endoscopic flow-passage confluent structure that connects a gas-feed tube and a liquid-feed tube provided in an endoscope to a confluent tube communicating with an ejection nozzle arranged at a tip of an insertion portion of the endoscope and for ejecting a cleaning fluid of the endoscope, the structure comprising:
   (i) a passage connection member which is formed by drilling a single unit having
      one end opened to be drilled with two upstream-passage receiving bores in which the gas-feed and liquid-feed tubes are respectively directly inserted and fixed,
      an other end opened to be drilled with one downstream-passage receiving bore, and an intermediate region that communicates the upstream-passage receiving bores with downstream-passage receiving bore and comprises a passage confluent hollow space having an inner diameter increasing in a taper-form in a direction of from the downstream-passage receiving bore toward the upstream-passage receiving bores by drilling from the downstream-passage receiving bores;

the passage connection member having an outer diameter and the outer diameter of the passage connection member is constant from said one end continuously through the intermediate region to the other end of the passage connection member; and (ii) a coupler pipe having one end inserted into the downstream-passage receiving bore and other end connected with a base of the confluent tube.

2. The endoscopic flow-passage confluent structure according to claim 1, wherein the passage connection member comprises a metal.

3. The endoscopic flow-passage confluent structure according to claim 1,
wherein the upstream-passage receiving bores have a diameter slightly greater than an outer diameter of the gas-feed tube and the liquid-feed tube, and the downstream-passage receiving bore has a diameter greater than an outer diameter of the confluent tube.

4. A method of making an endoscopic flow-passage confluent structure that connects a gas-feed tube and a liquid-feed tube provided in an endoscope to a confluent tube for communication with an ejection nozzle arranged at a tip of an insertion portion of the endoscope and for ejecting a cleaning fluid of the endoscope, the method comprising:

(i) forming a passage connection member by drilling a single unit having
one end drilled to form two upstream-passage receiving bores in which the gas-feed and liquid-feed tubes are respectively to be directly inserted and fixed,
an other end drilled to form one downstream-passage receiving bore, and
an intermediate region that communicates the upstream-passage receiving bores with the downstream-passage receiving bore and comprises a passage confluent hollow space having an inner diameter increasing in a taper-form in a direction from the downstream-passage receiving bore toward the upstream-passage receiving bores by drilling from the downstream-passage receiving bores;

the passage connection member being formed to have an outer diameter and the outer diameter of the passage connection member being constant from said one end continuously through the intermediate region to the other end of the passage connection member; and (ii) inserting one end of a coupler pipe into the downstream-passage receiving bore and connecting an other end of the coupler pipe with a base of the confluent tube.

* * * * *